(12) United States Patent  
Larkin

(10) Patent No.: US 8,323,211 B2
(45) Date of Patent: Dec. 4, 2012

(54) SEXUALLY TRANSMITTED INFECTION SAMPLING DEVICE

(76) Inventor: Daniel Larkin, St. Paul, MN (US)

(*) Notice: Subject to any disclaimer, the term of this patent is extended or adjusted under 35 U.S.C. 154(b) by 777 days.

(21) Appl. No.: 11/789,182

(22) Filed: Apr. 24, 2007

(65) Prior Publication Data

US 2007/0282222 A1 Dec. 6, 2007

Related U.S. Application Data

(63) Continuation-in-part of application No. 11/588,120, filed on Oct. 26, 2006, now Pat. No. 7,749,173.

(60) Provisional application No. 60/810,055, filed on Jun. 1, 2006.

(51) Int. Cl.
*A61B 10/00* (2006.01)

(52) U.S. Cl. .......................... 600/569; 600/572; 600/562

(58) Field of Classification Search .................. 600/562, 600/569, 570, 572
See application file for complete search history.

(56) References Cited

U.S. PATENT DOCUMENTS

| | | | |
|---|---|---|---|
| 2,767,703 A | 1/1956 | Nieburgs | |
| 3,815,580 A | 6/1974 | Oster | |
| 3,877,464 A | 4/1975 | Vermes | |
| 4,027,658 A | 6/1977 | Marshall | |
| 4,127,113 A | 11/1978 | Nollan | |
| 4,227,537 A | 10/1980 | Suciu et al. | |
| 4,361,151 A * | 11/1982 | Fitzgerald | 604/15 |
| 4,700,713 A | 10/1987 | Kist | |
| 4,754,764 A | 7/1988 | Bayne | |
| 4,762,133 A | 8/1988 | Bayne et al. | |
| 4,767,398 A * | 8/1988 | Blasius, Jr. | 604/1 |
| 4,873,992 A | 10/1989 | Bayne | |
| 4,981,143 A | 1/1991 | Sakita et al. | |
| D316,488 S | 4/1991 | Stormby | |
| 5,022,408 A | 6/1991 | Mohajer | |
| 5,084,005 A * | 1/1992 | Kachigian | 600/569 |
| 5,131,402 A | 7/1992 | Van Dooren | |
| 5,191,899 A * | 3/1993 | Strickland et al. | 600/569 |
| D335,706 S | 5/1993 | Mohajer | |
| 5,253,652 A | 10/1993 | Fast | |
| 5,279,307 A | 1/1994 | Mohajer | |
| 5,370,128 A | 12/1994 | Wainwright | |
| 5,445,164 A | 8/1995 | Worthen et al. | |
| 5,623,941 A | 4/1997 | Hedberg et al. | |
| 5,713,369 A | 2/1998 | Tao et al. | |
| 5,787,891 A * | 8/1998 | Sak | 600/572 |
| 6,013,036 A | 1/2000 | Caillouette | |
| D441,141 S | 4/2001 | Shalita | |

(Continued)

FOREIGN PATENT DOCUMENTS

EP 0448137 A1 1/1991

(Continued)

*Primary Examiner* — Brian Szmal
*Assistant Examiner* — H. Q. Nguyen
(74) *Attorney, Agent, or Firm* — Dicke, Billig & Czaja, PLLC

(57) ABSTRACT

A sexually transmitted infection (STI) sampling device includes an elongated shaft that defines a first end separated from a second end, and an absorbent sampler coupled to one of the first and second ends. The absorbent sampler includes an absorbent core disposed on a longitudinal axis of the elongated shaft, and a plurality of fibers extending from the absorbent core. The plurality of fibers is configured to exfoliate and capture cells from a tissue surface of a patient, and the absorbent core is configured to absorb exfoliated cells not captured by the fibers.

21 Claims, 14 Drawing Sheets

U.S. PATENT DOCUMENTS

| | | |
|---|---|---|
| 6,258,044 B1 | 7/2001 | Lonky et al. |
| 6,277,089 B1 | 8/2001 | Yoon |
| 6,343,608 B1 * | 2/2002 | Gueret .......................... 132/320 |
| 6,346,086 B1 | 2/2002 | Maksem et al. |
| 6,394,966 B1 | 5/2002 | Gill et al. |
| 6,409,681 B1 | 6/2002 | Caillouette |
| 6,612,996 B2 | 9/2003 | Williams |
| 6,623,440 B1 * | 9/2003 | Weldon ............................ 604/1 |
| 6,723,057 B1 | 4/2004 | Pearce |
| D500,410 S | 1/2005 | Dragan |
| D500,553 S | 1/2005 | George |
| 6,936,013 B2 * | 8/2005 | Pevoto ......................... 600/562 |
| 7,097,629 B2 | 8/2006 | Blair |
| 7,226,457 B2 | 6/2007 | Carson et al. |
| 2002/0032389 A1 | 3/2002 | Fournier |
| 2002/0068881 A1 | 6/2002 | Kobren et al. |
| 2004/0015300 A1 | 1/2004 | Ganguli et al. |
| 2004/0153000 A1 | 8/2004 | Pevoto |
| 2004/0236247 A1 | 11/2004 | Rizvi |
| 2005/0159721 A1 | 7/2005 | Yamamoto et al. |
| 2005/0256440 A1 * | 11/2005 | Zunker et al. ..................... 604/1 |
| 2005/0283129 A1 | 12/2005 | Hammons et al. |
| 2006/0142668 A1 | 6/2006 | Triva |

FOREIGN PATENT DOCUMENTS

| | | |
|---|---|---|
| GB | 2 208 603 | 4/1989 |
| WO | WO 91/16855 | 11/1991 |
| WO | WO 99/53841 | 10/1999 |

* cited by examiner

SEXUALLY TRANSMITTED INFECTION SAMPLING DEVICE

CROSS-REFERENCE TO RELATED APPLICATIONS

This Utility Patent Application is related to and claims the benefit of the filing date under 35 U.S.C. §120 as a continuation-in-part of the commonly assigned Utility patent application Ser. No. 11/588,120, filed on Oct. 26, 2006 now U.S. Pat. No. 7,749,173 entitled METHOD AND APPARATUS FOR SIMULTANEOUSLY COLLECTING EXOCERVICAL AND ENDOCERVICAL SAMPLES, which claimed the benefit of the filing date of U.S. Provisional Patent Application Ser. No. 60/810,055, filed Jun. 1, 2006, entitled "METHOD AND APPARATUS FOR SIMULTANEOUSLY COLLECTING EXOCERVICAL AND ENDOCERVICAL SAMPLES," both of which are incorporated herein by reference.

BACKGROUND

The Papanicolaou test ("Pap test" or Pap smear) has proven to be highly valuable in the early detection of cervical pre-cancerous and cancerous growths. The Pap test refers to the collection of cells from the cervical face, the endocervical canal, and occasionally from the vaginal wall. The collected cells are subsequently "smeared" onto a microscope plate or deposited and mixed into a broth and analyzed for evidence of pre-cancerous or cancerous growth. A periodic Pap test permits the early detection of malignant cells, which enables early palliative care in treating cervical pre-cancerous and cancerous growths.

One device that has been useful in collecting cells during a Pap test includes a wooden or plastic spatula. Such spatulas are inexpensive and can be effective at collecting cells from the cervical face. However, spatulas have proven to be less than effective in collecting adequate cell samples from the endocervical canal. This is a potentially serious short-coming, because any sample that does not include endocervical cells is deemed to be an inadequate Pap smear sample. That is to say, the proper interpretation and diagnosis of the state of the cells is inconclusive unless a sufficient number of cells are collected from the endocervical canal.

Other devices that are useful in collecting cells during Pap tests include cotton swabs and the like. In general, cell samples are collected by swabbing the exocervical wall and the endocervical canal with the swab. Although cotton swabs are associated with a somewhat improved collection/yield of cells, cotton swabs are not abrasive enough to scrap the endocervical canal and consistently retrieve an adequate, representative sample.

Certain bristle brushes have also proven useful in collecting cells during a Pap test. In this regard, the bristle brushes are capable of obtaining endocervical cells during sampling, however bristle brushes are abrasive, and their use can be uncomfortable and increase the incidence of patient bleeding.

Pap tests have proven to be useful in the early detection of malignant cells and are related to a reduction in the incidence and death rate due to cervical cancers. Improvements to sampling devices useful in collecting cells during Pap tests will be welcomed by the medical community and patients alike.

SUMMARY

One embodiment provides a combination exo-endocervical sampling device that includes a shaft, a sampler, and a combination exo-endocervical sampler. The shaft defines a first end opposite a second end, a transverse break line between the first and second ends, and a textured surface adjacent to the break line. The sampler is coupled to the first end, and the combination exo-endocervical sampler is coupled to the second end. The combination exo-endocervical sampler includes a pair of opposing wings disposed transverse to the shaft, and a brush that extends from the wings along a central axis of the shaft. In this regard, each of the opposing wings includes a sampling surface having a staggered array of beads, and the brush includes a multiplicity of looped fibers, where each looped fiber includes a first closed end opposite a second closed end such that the closed ends extend transverse from the central axis of the shaft.

Another embodiment of the present invention provides a combination exo-endocervical sampling device that includes a shaft, and a combination exo-endocervical sampler coupled to the shaft. The combination exo-endocervical sampler includes a pair of opposing wings disposed transverse to the shaft and a prominence extending from the wings along a central axis of the shaft. In this regard, the opposing wings define a first sampling surface and the prominence includes a second sampling surface, at least one of the first and second sampling surfaces characterized by an absence of bristles and defining a void space configured to capture exo-endocervical cells.

Another embodiment of the present invention provides a combination exo-endocervical sampling device. The device includes a shaft, a sampler coupled to an end of the shaft, and a combination exo-endocervical sampler coupled to another end of the shaft. The shaft defines a transverse break line between the ends, and a textured surface adjacent to the break line. The sampler includes one of a swab or a spatula. The combination exo-endocervical sampler includes a pair of opposing wings disposed transverse to the shaft and a prominence extending from the wings along a central axis of the shaft. In this regard, the opposing wings define a first sampling surface and the prominence includes a second sampling surface, at least one of the first and second sampling surfaces including a multiplicity of endless fibrils defining a void space therebetween configured to capture exo-endocervical cells.

Another embodiment of the present invention provides a method of simultaneously collecting exocervical and endocervical cells from a female patient. The method includes providing a combination exo-endocervical sampling device including a sampler having a pair of opposing wings and a prominence extending from the wings, at least one of the opposing wings and the prominence including a multiplicity of looped fibers defining a void space therebetween configured to capture exo-endocervical cells. The method additionally includes placing the sampling device in contact with a cervix of the female patient. The method further includes collecting exocervical cells with the opposing wings of the sampling device, and simultaneously collecting endocervical cells with the prominence.

Another embodiment provides a sexually transmitted infection (STI) sampling device. The STI device includes an elongated shaft that defines a first end separated from a second end, and an absorbent sampler coupled to one of the first and second ends. The absorbent sampler includes an absorbent core disposed on a longitudinal axis of the elongated shaft, and a plurality of fibers extending from the absorbent core. The plurality of fibers is configured to exfoliate and capture cells from a tissue surface of a patient, and the absorbent core is configured to absorb exfoliated cells not captured by the fibers.

Another embodiment provides a sexually transmitted infection (STI) sampling device that includes an elongated shaft that defines a first end separated from a second end, and a sampler coupled to one of the first and second ends. The sampler includes means for exfoliating cells from a tissue surface of a patient, and means for absorbing exfoliated cells that is separate from the means for exfoliating cells.

Another embodiment provides a method of collecting a sexually transmitted infection biological sample. The method includes contacting genital tissue of a patient with an absorbent sampler including an absorbent core and a plurality of fibers extending from the absorbent core. The method additionally includes exfoliating cells with the fibers, capturing with the fibers a portion of the cells exfoliated by the fibers, and capturing with the absorbent core an additional portion of the cells exfoliated by the fibers.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of the embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1A:
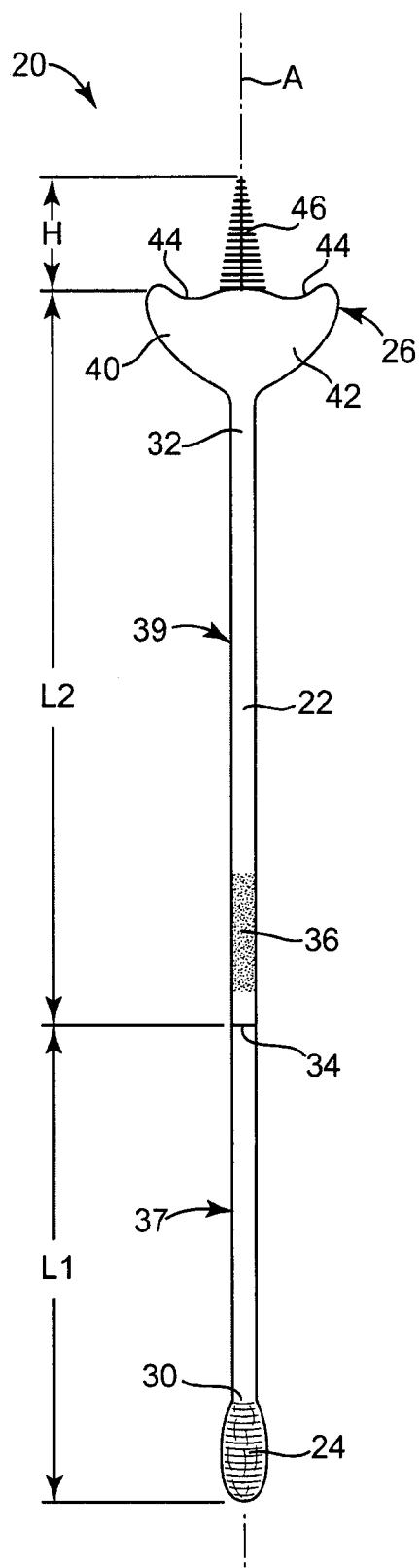
FIG. 1A illustrates a front view of a combination exo-endocervical sampling device according to one embodiment of the present invention.

FIG. 1A illustrates a front view of a combination exo-endocervical sampling device 20 according to one embodiment of the present invention. Combination exo-endocervical sampling device 20 includes a shaft 22, a sampler 24, and a combination exo-endocervical sampler 26. As a point of reference, shaft 22 and sampling device 20 are aligned along a central axis A. Central axis A is a major, or longitudinal, axis of sampling device 20.

Although combination exo-endocervical sampling device 20 is not typically employed in a sterile field when cell samples are collected, one embodiment provides for combination exo-endocervical sampling device 20 to be sterilized or sterilizable. In any regard, combination exo-endocervical sampling device 20 is provided with a reduced bio-load that does not disrupt cell sampling or analysis.

Shaft 22 defines a first end 30 opposite a second end 32, a transverse break line 34 between the first end 30 and the second 32, and a textured surface 36 adjacent to break line 34. In one embodiment, shaft 22 is integrally formed of molded plastic. Suitable molded plastics for shaft 22 include thermoplastic materials in general, and medical grade polyolefins including polypropylene and polyethylene in particular.

In one embodiment, shaft 22 defines a first portion 37 that extends from break line 34 to sampler 24, and a second portion 39 that extends from break line 34 to combination exo-endocervical sampler 26. In one embodiment, textured surface 36 is disposed on second portion 39 adjacent to break line 34. In this regard, when shaft 22 is severed at break line 34, sampler 24 defines a distal end of first portion 37. In a similar manner, when shaft 22 is severed at break line 34, combination exo-endocervical sampler 26 defines a distal end of second portion 39. In one embodiment, break line 34 is approximately centered within textured surface 36.

In one embodiment, first portion 37 defines a length L1 between about 5 to 7 cm, and preferably the length L1 of first portion 37 is about 6.5 cm. In one embodiment, second portion 39 defines a length L2 that is between about 16 to 20 cm, preferably about 18 cm.

Figure 4:
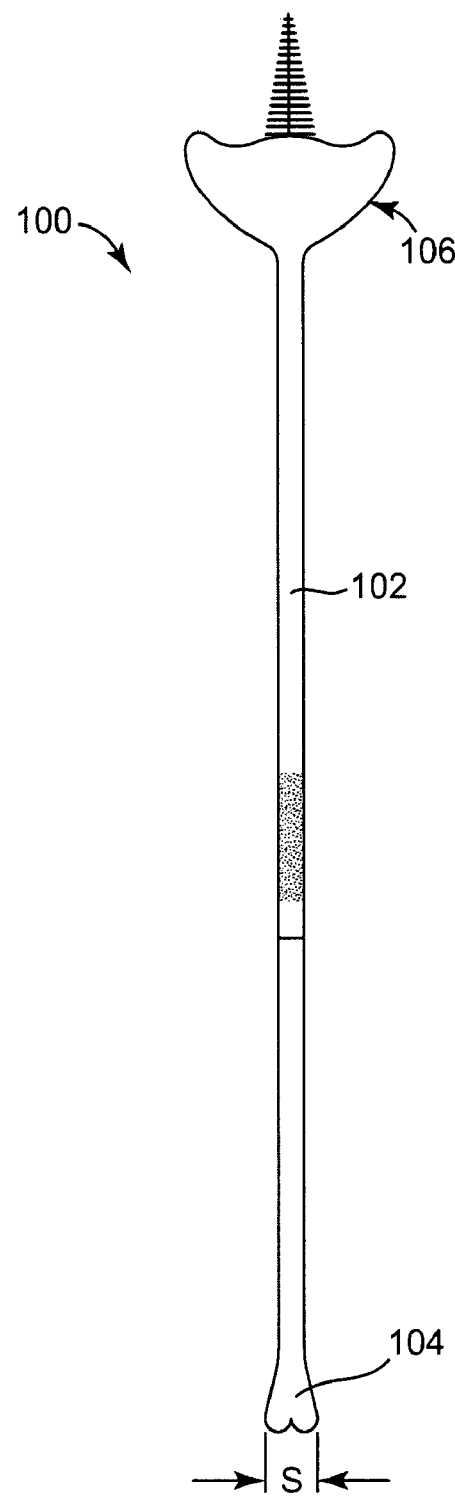
FIG. 4 illustrates a front view of another combination exo-endocervical sampling device according to one embodiment of the present invention.

Sampler 24 is coupled to first end 30. In one embodiment, sampler 24 includes a cotton-tipped swab. In another embodiment, sampler 24 is a rigid spatula (as best illustrated in FIG. 4).

Combination exo-endocervical sampler 26 is coupled to second end 32 of shaft 22. Combination exo-endocervical sampler 26 includes a pair of opposing wings 40, 42 that are disposed transverse to shaft 22 (i.e., transverse to central axis A), and a brush 46 that extends away from the wings 40, 42 along the central axis A of shaft 22. The wings 40, 42 combine to define a generally curved sampling surface 44 separate from a sampling surface area provided by brush 46.

In one embodiment, brush 46 defines a height H between about 1 to 3 cm, and preferably the height H of brush 46 is about 1.5 cm when sampling device 20 is employed in a Pap test on a non-parous patient, and height H of brush 46 is about 2 cm when sampling device 20 is employed in a Pap test for a parous patient.

The sampler 24 and the combination exo-endocervical sampler 26 of the combination exo-endocervical sampling device 20 enable the simultaneous collection of cells during Pap test procedures and wet prep procedures through the use of a single device 20.

As employed herein, parous means a patient who has given birth vaginally one or more times. The terms non-parous and nulli-parous mean a woman who has never given birth vaginally. Pregnant means a patient carrying developing offspring within the body, and in particular within the uterus. Stenotic means a constriction or narrowing of a canal and in particular, a constriction or narrowing of the cervical canal.

Figure 1B:
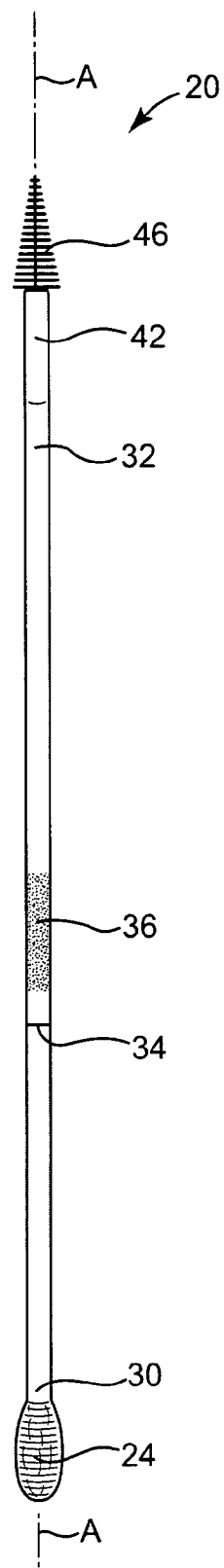
FIG. 1B illustrates a side view of the combination exo-endocervical sampling device illustrated in FIG. 1A.

FIG. 1B illustrates a right side view of combination exo-endocervical sampling device 20 according to one embodiment of the present invention. In one embodiment, at least a portion of brush 46 defines a diameter that is wider than a thickness of wing 42. In other words, portions of brush 46 extend transverse to the central axis A and are wider than the wings 40, 42 are thick.

Figure 1C:
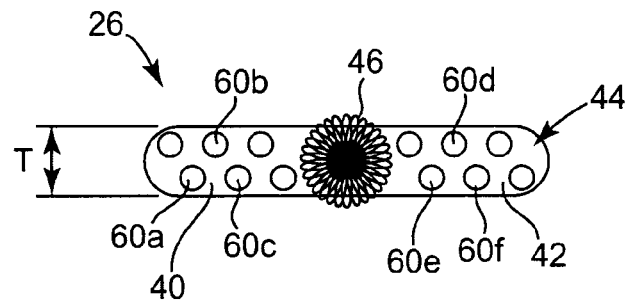
FIG. 1C illustrates a top view of a combination exo-endocervical sampler according to one embodiment of the present invention.
Figure 2:
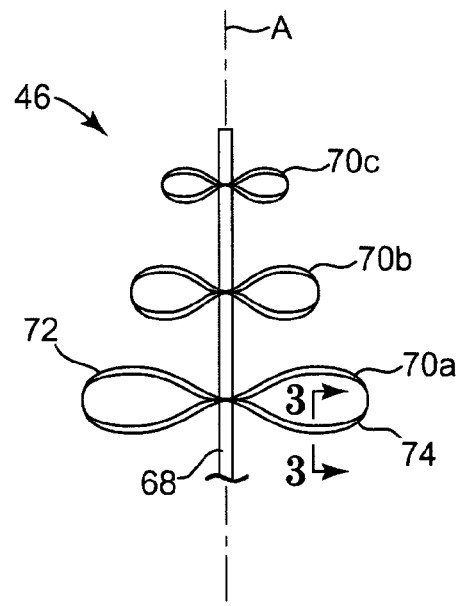
FIG. 2 illustrates a perspective view of a brush portion of a combination exo-endocervical sampler according to one embodiment of the present invention.

FIG. 1C illustrates a top view of exo-endocervical sampler 26 according to one embodiment of the present invention. In one embodiment, exo-endocervical sampler 26 includes rigid, molded wings 40, 42 and a flexible brush 46 formed from looped fibers (as best illustrated in FIG. 2). Wings 40, 42 define a thickness T that is between about 1.5 to 5 mm, and preferably thickness T is between about 2 to 4 mm. In one embodiment, wings 40, 42 extend transverse to the central axis A (FIG. 1A) and combine to define sampling surface 44. Wings 40, 42 are molded from a plastic, such as thermoplastic polyolefin including polyethylene, polypropylene, polyester, nylon, or "soft" polymers including block co-polymers such as block co-polyesters. In general, wings 40, 42 are molded from plastics that are FDA approved for medical devices.

Sampling surface 44 is provided to atraumatically scrape a face portion of a cervix to collect exocervical cells. In one embodiment, sampling surface 44 includes an array of beads 60a, 60b, 60c, 60d, 60e, 60f that project from sampling surface 44 by between about 1-2 mm. In one embodiment, the array of beads 60a, 60b, 60c, 60d, 60e, 60f is a staggered array of alternating beads, as illustrated. It is to be understood that other patterns of arranging 60a, 60b, 60c, 60d, 60e, 60f are also acceptable, and other suitable arrangements of beads is contemplated. In addition, although beads 60a, 60b, 60c, 60d, 60e, 60f are illustrated as circular, other shapes and conformations of beads 60a, 60b, 60c, 60d, 60e, 60f are contemplated. Sampling surface 44 and beads 60a, 60b, 60c, 60d, 60e, 60f combine to atraumatically collect, or sample, exo-cervical cells during a Pap test procedure.

FIG. 2 illustrates a perspective, simplified view of brush 46 according to one embodiment of the present invention. In general, brush 46 is provided to atraumatically collect endocervical cell samples. Brush 46 includes multiple loops of fibers 70, only three of which are illustrated in the simplified view. It is to be understood that brush 46 includes many multiples of loops of fibers 70. In this regard, in one embodiment the multiple loops of fibers 70 are wound in a helical fashion. In another embodiment, the multiple loops of fibers 70 are wound and uniformly spaced in a symmetric "Christmas tree" configuration. In any regard, the loops of fibers 70 do not terminate in an end, as is commonly associated with a bristle of a bristle-styled brush. Bristles of a bristle brush have the potential to damage cells as they are collected. In contrast, the endless loops of fibers 70 atraumatically collect exo-endocervical and retain the cells in a void space defined between the loops of fibers 70.

Brush 46 includes a semi-rigid or rigid strand 68, and looped fibers 70a, 70b, and 70c that are coupled to strand 68. Strand 68 is generally oriented along central axis A, and looped fibers 70a, 70b, and 70c generally extend transverse to strand 68 and central axis A. In one embodiment, strand 68 includes two twined or twisted strands wrapped to capture looped fibers 70a, 70b, and 70c. Strand 68 includes corrosion resistant metal, such as stainless steel. Alternatively, strand 68 is formed from plastic materials, such as nylon or polyester. In one embodiment, each looped fiber includes a first closed end 72 opposite a second closed end 74, and the closed ends 72, 74 extend transverse from the central axis A.

The open spaces between the closed loop ends 72, 74 provide a first means to atraumatically collect endocervical cell samples. Looped fibers 70a, 70b, and 70c capture and retain cervical cell samples between loop ends 72, 74. In contrast to the known bristle brushes that have bristle ends (i.e. end-on bristles), looped fibers 70a, 70b, and 70c do not have bristle ends that can potentially puncture or otherwise damage tissue. Significantly, looped fibers 70a, 70b, and 70c are provided with closed loop ends 72, 74 that present a lower puncture/trauma risk to tissue when compared to end-on bristles of the known cervical brushes.

Figures 3A, 3B:
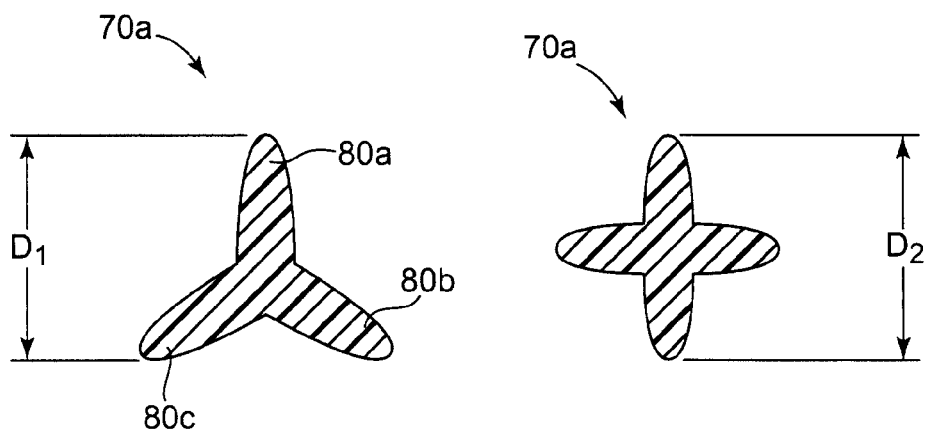
FIG. 3A illustrates a cross-sectional view of a fiber of the brush portion illustrated in FIG. 2.
FIG. 3B illustrates a cross-sectional view of another fiber for the brush portion illustrated in FIG. 2 according to one embodiment of the present invention.

FIG. 3A illustrates a cross-sectional view of looped fiber 70a according to one embodiment of the present invention. In one embodiment, looped fiber 70a defines a transverse cross-section that is tri-lobal. For example, looped fiber 70a includes a first lobe 80a, a second lobe 80b, and a third lobe 80c.

In one embodiment, looped fiber 70a defines an effective diameter D1 of between about 50 micrometers (microns) to about 1,000 microns. Diameter and effective diameter are terms that are used broadly in this Specification to define the outermost planform (or perimeter) of an object viewed in cross-section. Diameter, as used herein, is not limited to circular objects. In particular, shaped looped fibers, such as fiber 70a, define a perimeter that is non-circular.

The open area between each lobe 80a, 80b, 80c defines a trough that is suitable for the atraumatic collection of cervical cells. Looped fiber 70a defines a non-circular perimeter in transverse cross-section that is configured for atraumatic collection of cervical cells in a Pap test procedure. In this regard, the surfaces of looped fiber 70a are suited to abrade portions of the endocervical canal to remove cervical cells for sampling without traumatizing the surface from which the cells are removed, and without damaging the collected cells. The cross-sectional non-circular shape of looped fibers 70 provide a second means for atraumatically collecting endocervical cell samples.

Suitable fibers and equipment to produce suitable fibers are available from, for example, Hills, Inc., W. Melbourne, Fla. Other suitable fibers are shaped fibers available from Du Pont, Wilmington, Del. One such suitable fiber is a mushroom-shaped bicomponent fiber identified as a 3GT fiber available from Du Pont-Torray Co., as marketed by Du Pont-Torray Co., Ltd., and available through Du Pont in Wilmington, Del.

FIG. 3B illustrates a cross-sectional view of another looped fiber 70a. In one embodiment, looped fiber 70a is X-shaped in transverse cross-section. In another embodiment, looped fiber 70a is cross-shaped in transverse cross-section. In this regard, X-shaped looped fiber 70a defines an effective diameter D2 that is between about 50 to 1,000 microns. The open areas illustrated between legs of the X-shaped fiber 70a form troughs that are suitable for atraumatic collection of cervical cells in a Pap test procedure, as described above.

Suitable materials for forming/extruding shaped looped fibers 70 include polyolefins in general and thermoplastic polymers such as nylon, or polyester in particular.

FIG. 4 illustrates a front view of another combination exo-endocervical sampling device 100 according to one embodiment of the present invention. Combination exo-endocervical sampling device includes a shaft 102, a sampler 104, and a combination exo-endocervical sampler 106. In general, shaft 102 and exo-endocervical sampler 106 are similar to shaft 22 and exo-endocervical sampler 26, respectively, illustrated in FIG. 1A above.

In one embodiment, sampler 104 includes a molded plastic spatula that defines a width S of between about 0.5 to 2 cm, and preferably width S is about 0.75 cm. In one embodiment, molded plastic spatula sampler 104 is integrally formed with shaft 102 of a molded plastic, such as, for example, polyethylene. Sampler 104 is suitable for atraumatic collection of cervical cells from a face of a cervix and/or cells from a vaginal wall, for example, during a Pap test procedure.

Figures 5A, 5B:
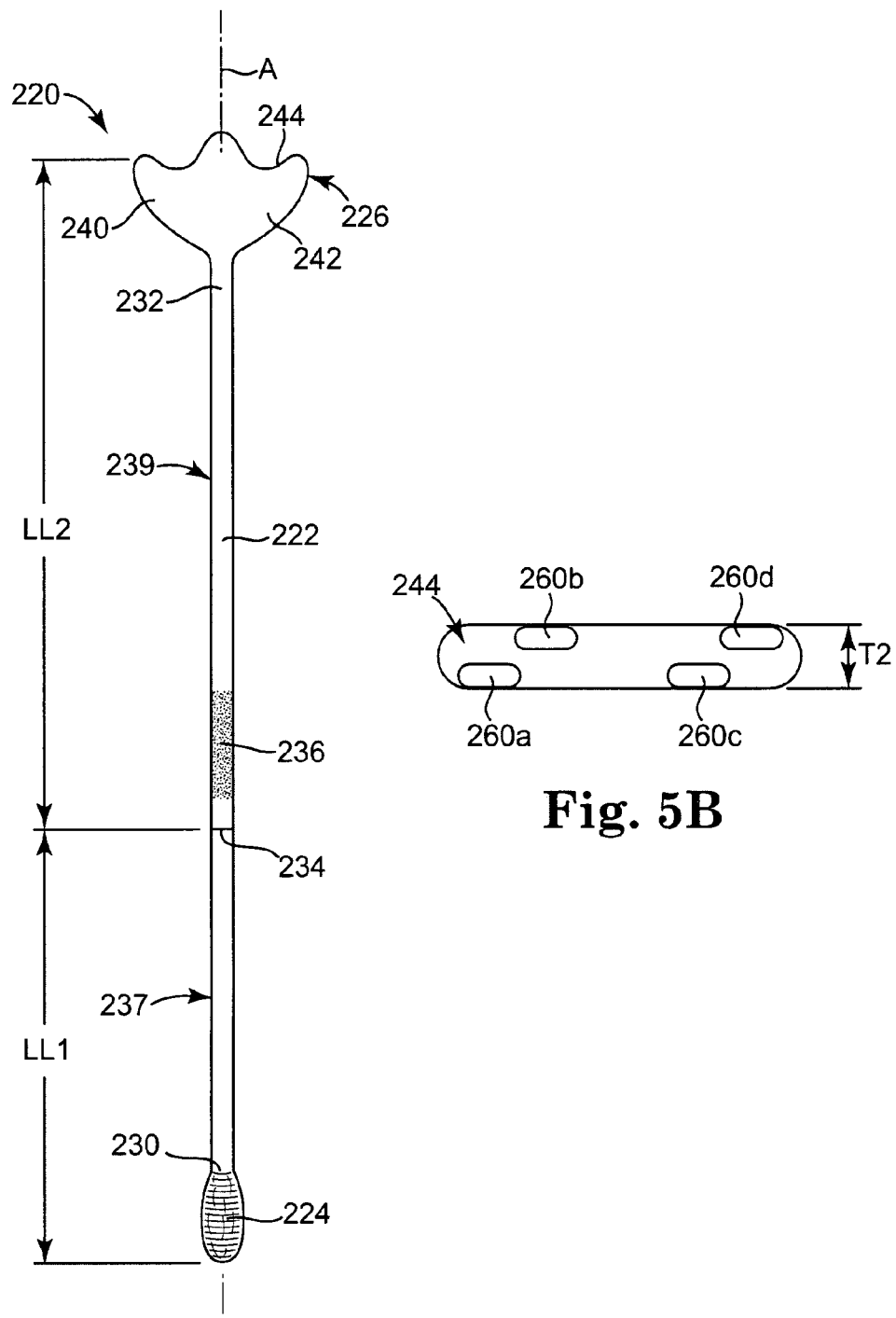
FIG. 5A illustrates a front view of an exocervical sampling device according to one embodiment of the present invention.
FIG. 5B illustrates a top view of one end of the exocervical sampling device illustrated in FIG. 5A.

FIG. 5A illustrates a front view of an exocervical sampling device 220 according to one embodiment of the present invention. In one embodiment, exocervical sampling device 220 is configured for cervical cell sampling of a pregnant patient and includes a shaft 222, a sampler 224, and an exocervical sampler 226. In one embodiment, exocervical sampling device 220 is sterilized or sterilizable, similar to device 20 above.

Shaft 222 defines a first end 230 opposite a second end 232, a transverse break line 234 between the first end 230 and the second 232, and a textured surface 236 adjacent to break line 234. In one embodiment, shaft 222 is integrally formed of molded plastic. Suitable molded plastics for shaft 222 include thermoplastic materials in general, and medical grade plastics including polypropylene and polyethylene in particular.

In one embodiment, shaft 222 defines a first portion 237 that extends from break line 234 to sampler 224, and a second portion 239 that extends from break line 234 to combination exo-endocervical sampler 226. In one embodiment, textured surface 236 is disposed on second portion 239 adjacent to break line 234. In this regard, when shaft 222 is severed at break line 234, sampler 224 defines a distal end of first portion 237. In a similar manner, when shaft 222 is severed at break line 234, combination exo-endocervical sampler 226 defines a distal end of second portion 239. In another embodiment, textured surface 236 spans either side of break line 234.

In one embodiment, first portion 237 defines a length LL1 between about 5 to 7 cm, and preferably the length LL1 of first portion 237 is about 6.5 cm. In one embodiment, second portion 239 defines a length LL2 that is between about 16 to 20 cm, preferably about 16.5 cm.

Sampler 224 is coupled to first end 230. In one embodiment, sampler 224 is a mat of fibers, such as are provided in a cotton-tipped swab. In another embodiment, sampler 224 is a rigid spatula (similar to spatula 104 illustrated in FIG. 4).

Exocervical sampler 226 is coupled to second end 232 of shaft 222. Exocervical sampler 226 includes a pair of opposing wings 240, 242 that are disposed transverse to shaft 222 (i.e., transverse to central axis A) and are curved to correspond to a shape compatible with an exterior surface of the cervix. The wings 240, 242 combine to define a sampling surface 244.

FIG. 5B illustrates a top view of exocervical sampler 226 according to one embodiment of the present invention. Wings 240, 242 define a thickness T2 that is between about 1.5 to 5 mm, and preferably thickness T2 is between about 2 to 4 mm. In one embodiment, wings 240, 242 extend transverse to the central axis A (FIG. 1A) and combine to define sampling surface 244.

Sampling surface 244 is provided to atraumatically scrape a face portion of a cervix of a pregnant patient to collect exocervical cells. In one embodiment, sampling surface 244 includes an array of beads 260a, 260b, 260c, 260d that project above sampling surface 244. In one embodiment, array of beads 260a, 260b, 260c, 260d is a staggered array, although other arrangements for beads 260a, 260b, 260c, 260d are also acceptable. Beads 260a, 260b, 260c, 260d are illustrated as cylinders, although other shapes are also acceptable. Sampling surface 244 and beads 260a, 260b, 260c, 260d combine to atraumatically collect, or sample, exocervical cells from a face of a cervix of a pregnant patient during a Pap test procedure.

In one embodiment, wings 240, 242 are molded from a plastic, such as thermoplastic polymers including polyethylene, polypropylene, polyester, nylon, or "soft" polymers including block co-polymers such as block co-polyesters. In general, wings 240, 242 are molded from plastics that are FDA approved for medical devices.

In another embodiment, wings 240, 242 include a lofted intertwined mat of endless fibers that form a surface that is characterized by a random collection of interconnecting fibrils, as more fully described below in FIG. 9A.

Figure 6:
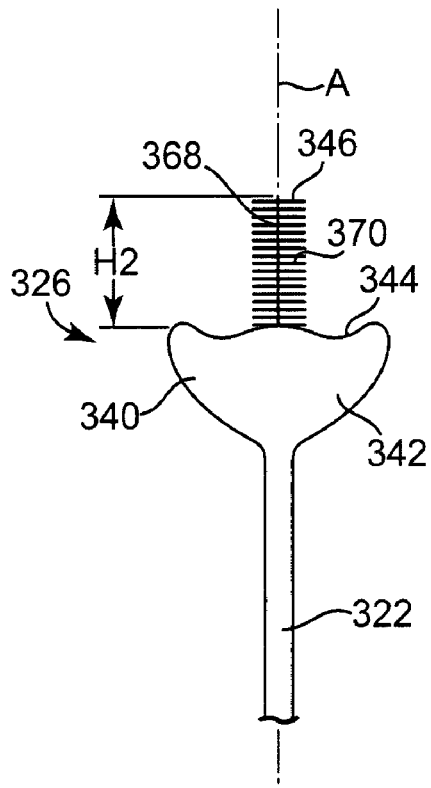
FIG. 6 illustrates a front view of another combination exo-endocervical sampler according to one embodiment of the present invention.

FIG. 6 illustrates a front view of another combination exo-endocervical sampler 326 according to one embodiment of the present invention. Combination exo-endocervical sampler 326 includes a pair of opposing wings 340, 342 that are disposed transverse to shaft 322 (i.e., transverse to central axis A), and a brush 346 that extends away from the wings 340, 342 along the central axis A of shaft 322. The wings 340, 342 combine to define a sampling surface 344 separate from a sampling surface area provided by brush 346.

In one embodiment, brush 346 is substantially cylindrical in shape and defines a height H2 between about 1 to 3 cm, and preferably the height H2 of brush 346 is about 1.5 cm when sampler 326 is employed in a Pap test on a non-parous patient, and height H2 of brush 346 is about 2 cm when sampler 326 is employed in a Pap test for a parous patient.

Brush 346 includes multiple loops of fibers 370. Brush 346 includes a semi-rigid or rigid strand 368, and looped fibers 370 that are coupled to strand 368. Strand 368 is generally oriented along central axis A, and looped fibers 370 generally extend transverse to strand 368 and central axis A. In one embodiment, strand 368 includes two twined or twisted strands wrapped to capture looped fibers 370.

Strand 368 includes corrosion resistant metal, such as stainless steel. Alternatively, strand 368 is formed from plastic materials, such as nylon. In one embodiment, each looped fiber includes a first closed end opposite a second closed end, and the closed ends extend transverse from the central axis A, in a manner similar to that illustrated in FIG. 2.

Fibers 370 are similar to the fibers illustrated in FIGS. 2 and 3A and 3B. In this regard, fibers 370 are looped and can include a non-circular perimeter in transverse cross-section that is configured for atraumatic collection of cervical cells in a Pap test procedure. Looped fibers 370 are suited to abrade portions of the endocervical canal to remove cervical cells for sampling without traumatizing the surface from which the cells are removed.

Figure 7:
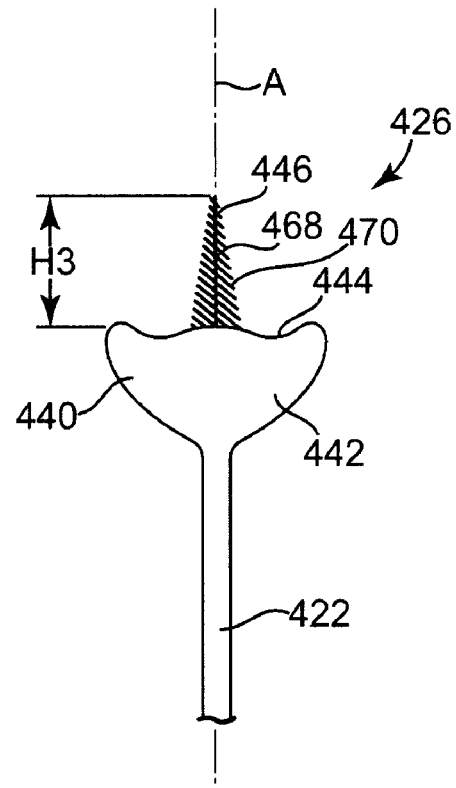
FIG. 7 illustrates a front view of another combination exo-endocervical sampler according to one embodiment of the present invention.

FIG. 7 illustrates a front view of another embodiment of a combination exo-endocervical sampler 426 according to one embodiment of the present invention. Combination exo-endocervical sampler 426 includes a pair of opposing wings 440, 442 that are disposed transverse to shaft 422 (i.e., transverse to central axis A), and a brush 446 that extends away from the wings 440, 442 along the central axis A of shaft 422. The wings 440, 442 combine to define a sampling surface 444 separate from a sampling surface area provided by brush 446.

In one embodiment, brush 446 is substantially conical in shape and defines a height H3 between about 1 to 3 cm, and preferably the height H3 of brush 446 is about 1.5 cm when sampler 426 is employed in a Pap test on a non-parous patient, and height H3 of brush 446 is about 2 cm when sampler 426 is employed in a Pap test for a parous patient.

Brush 446 includes multiple loops of fibers 470 wound conically in a helical fashion about a semi-rigid or rigid strand 468. Strand 468 is generally oriented along central axis A, and looped fibers 470 generally extend transverse to strand 468 and central axis A. In one embodiment, strand 468 includes two twined or twisted strands wrapped to capture looped fibers 470.

Strand 468 includes corrosion resistant metal, such as stainless steel. Alternatively, strand 468 is formed from plastic materials, such as nylon. In one embodiment, each looped fiber includes a first closed end opposite a second closed end, and the closed ends extend transverse from the central axis A, in a manner similar to that illustrated in FIG. 2.

Fibers 470 are similar to the fibers illustrated in FIGS. 2 and 3A and 3B. In this regard, fibers 470 are looped and can include a non-circular perimeter in transverse cross-section that is configured for atraumatic collection of cervical cells in a Pap test procedure. Looped fibers 470 are suited to abrade portions of the endocervical canal to remove cervical cells for sampling without traumatizing the surface from which the cells are removed.

Figure 8:
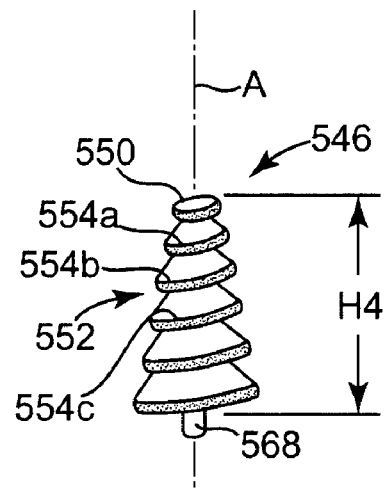
FIG. 8 illustrates a perspective view of another brush portion of a combination exo-endocervical sampler according to one embodiment of the present invention.

FIG. 8 illustrates a perspective view of a brush 546 according to one embodiment of the present invention. Brush 546 is usefully employed on any one of the combination exo-endocervical samplers 26, 106, 326, and 426 illustrated above.

In one embodiment, brush 546 is substantially conical in shape and defines a height H4 between about 1 to 3 cm, and preferably the height H4 of brush 546 is about 1.5 cm when employed in a Pap test on a non-parous patient, and height H4 of brush 546 is about 2 cm when employed in a Pap test for a parous patient.

Brush 546 includes a sponge 550 that defines a helical surface 552 wound about a semi-rigid or rigid strand 568. In one embodiment, sponge 550 is an open celled absorbent sponge formed of natural or synthetic cellulose or its derivatives, or of polymers. In another embodiment, sponge 550 is a closed cell sponge form of polyurethane or the like. Strand 568 is generally oriented along central axis A, and includes corrosion resistant metal, such as stainless steel. Alternatively, strand 568 is formed from plastic materials, such as nylon.

Helical surface 552 includes helically spaced ledges 554a, 554b, and 554c. Helical surface 552 is suited to abrade portions of the endocervical canal to remove cervical cells for sampling without traumatizing the surface from which the cells are removed.

In one embodiment, brush 546 includes a pair of opposing wings defined by helical surfaces 552 that are disposed transverse to the strand 568, and a prominence defined by top 550 of sponge. Prominence, or top 550 of sponge, extends from the wings 552 along a central axis A of the strand 568. In this regard, the opposing wings 552 define a first sampling surface and the prominence 550 defines a second sampling surface. The sponge 550 is characterized by an absence of bristles and defines pores or a void space within the sponge 550 that is configured to capture exo-endocervical cells.

Figure 9A:
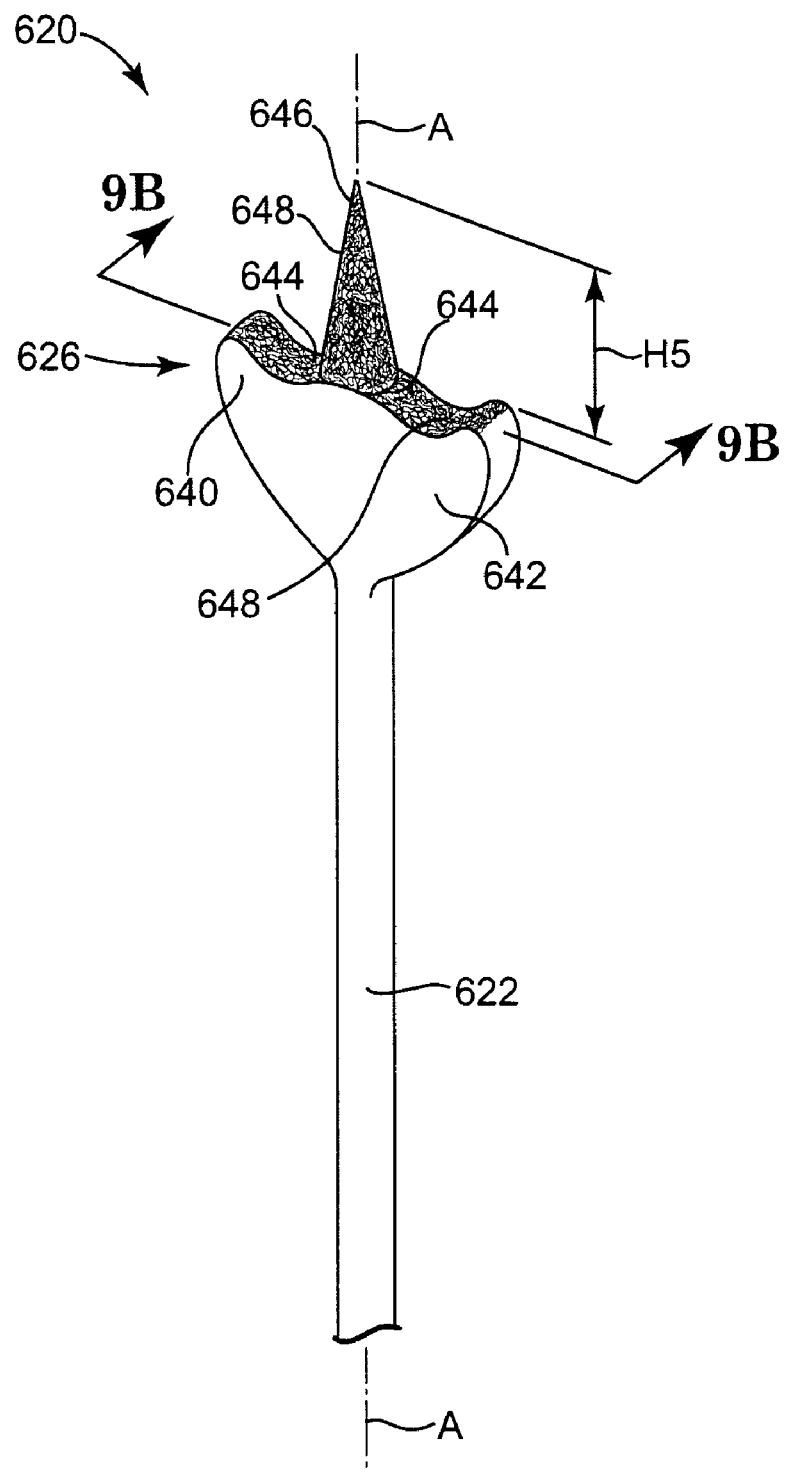
FIG. 9A illustrates a perspective view of another combination exo-endocervical sampling device according to one embodiment of the present invention.

FIG. 9A illustrates a perspective view of another combination exo-endocervical sampling device 620 according to one embodiment of the present invention. Combination exo-endocervical sampling device 620 includes a shaft 622, and a combination exo-endocervical sampler 626 extending from shaft 622 and aligned along a central longitudinal axis A. In one embodiment, a separate sampler such as a swab or a spatula is coupled to shaft 622 opposite sampler 626 in a manner similar to that illustrated in FIG. 1A (swab) or FIG. 4 (spatula).

Combination exo-endocervical sampler 626 includes a pair of opposing wings 640, 642 that are disposed transverse to shaft 622 (i.e., transverse to central axis A), and a prominence 646 that extends away from the wings 640, 642 along the central axis A of shaft 622. The prominence 646 and wings 640, 642 combine to define a sampling surface 644. In one embodiment, sampling surface 644 is covered at least partially by a lofted intertwined mat 648 of looped fibers that is suitable for the collection of cells from the cervical face and/or the endocervical canal.

In one embodiment, prominence 646 is substantially conical in shape and defines a height H5 between about 1 to 3 cm, and preferably the height H5 of prominence 646 is about 1.5 cm when sampler 626 is employed in a Pap test on a non-parous patient, and height H5 of prominence 646 is about 2 cm when sampler 626 is employed in a Pap test for a parous patient.

Lofted intertwined mat 648 of fibers forms a surface that is characterized by a random collection of interconnecting fibrils. The interconnecting fibrils define open spaces between the fibrils. The fibrils and the opens spaces combine to create a "lofty" structure that is useful in the atraumatic collection of cervical cells in a Pap test procedure. The looped fibrils may be referred to as "endless" fibers or fibrils, as individual fibrils forming the lofted intertwined mat 648 are formed to have no distinct "beginning" or "end" (i.e., the fibrils are not bristles). The lofted intertwined mat 648 is suited to abrade portions of the endocervical canal to remove cervical cells for sampling, and the open spaces between fibrils gather/retain the cells and minimize trauma to the cells as the cells are removed from the patient.

Figure 9B:
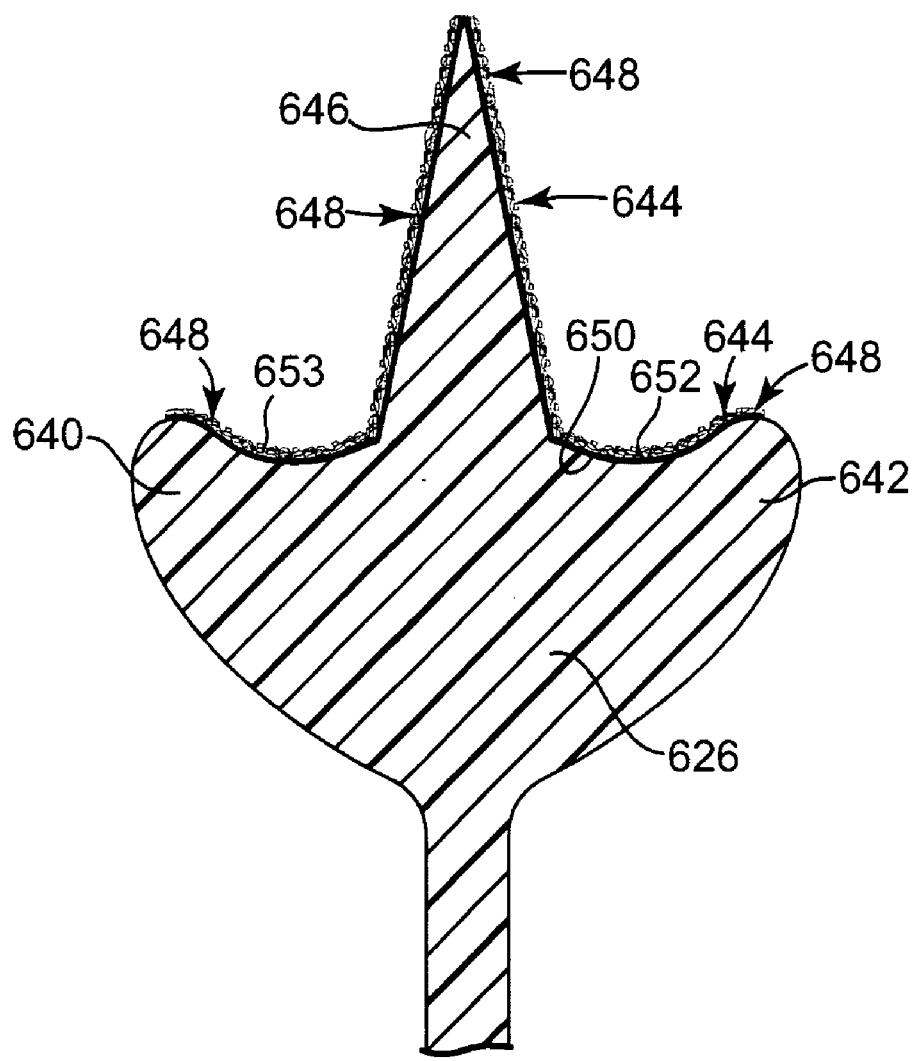
FIG. 9B illustrates a cross-sectional view of a combination exo-endocervical sampler of the device illustrated in FIG. 9A.

FIG. 9B illustrates a cross-sectional view of combination exo-endocervical sampler 626. Wings 640, 642 and prominence 646 are covered by lofted intertwined mat 648 of fibers. In one embodiment, lofted intertwined mat 648 of fibers includes a base 650 and intertwined fibers 652 extending from base 650. In one embodiment, lofted intertwined mat 648 of fibers is formed by extruding fibers 652 from a strand die onto a carrier web, or base 650. In an alternative embodiment, lofted intertwined mat 648 of fibers is formed by extruding fibers 652 from a strand die onto a moving conveyor belt, where the speed of the conveyor belt is selected to enable a portion of fibers 652 to cool into a continuous polymeric base 650, and another portion of fibers 652 becomes randomly tangled and intertwined as they cool on top of base 650. In this manner, a single process is employed to form base 650 and intertwine fibers 652. By an appropriate selection of fiber extrusion rate and collection speed, the mat of randomly intertwined fibers 652 will extend a distance from base 650 to provide a lofty structure. Between each of the randomly intertwined fibers 652, a void or space 653 is defined that is suited for the collection of cervical cell samples.

In one embodiment, base 650 and intertwined fibers 652 are formed from a thermoplastic polymeric material. Preferably, thermoplastic polymeric material is flexible, soft, and suited for medical applications. Examples of suitable thermoplastic materials include polyurethane, polyolefins, and polyolefins including a soft fraction of another polymer, for example, polybutylene. In one embodiment, after forming base 650 and intertwined fiber 652, lofted intertwined mat 648 of "endless" fibers is thermo-formed onto sampler 626 to cover wings 640, 642 and prominence 646.

Figure 10:
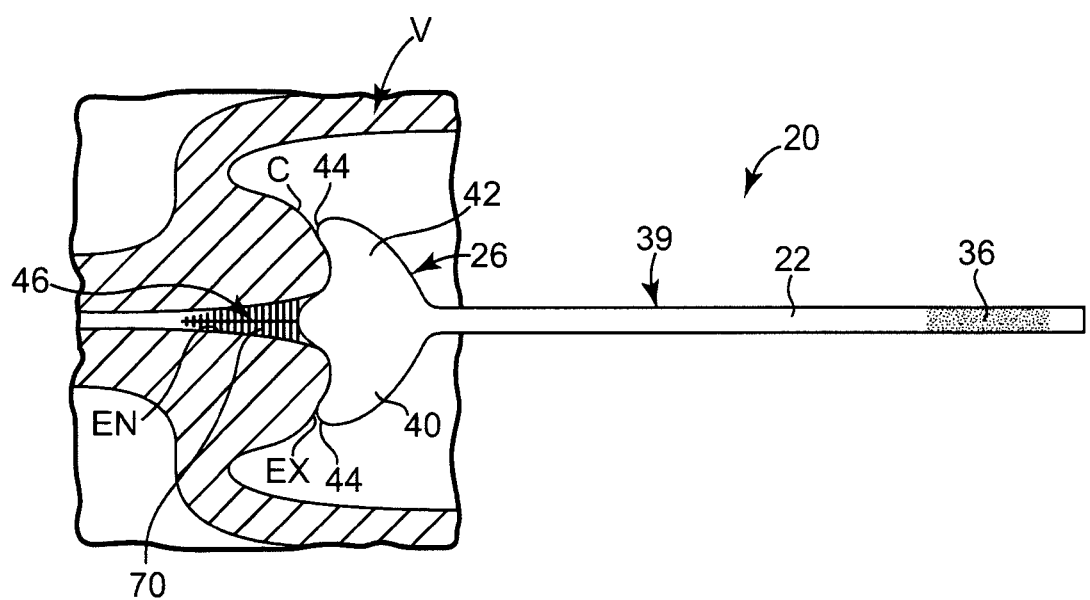
FIG. 10 illustrates a cross-sectional view of a combination exo-endocervical sampling device employed to simultaneously collect exocervical and endocervical cells.

FIG. 10 illustrates a cross-sectional view of combination exo-endocervical sampling device 20 employed to collect cervical cells from a cervix during a Pap test according to one embodiment of the present invention.

With reference to FIG. 1A, second portion 39 of combination exo-endocervical sampling device 20 has been severed from first portion 37. First portion 37 including sampler 24 (FIG. 1A) is provided to permit the clinician to collect a sample of cells from a wall of vagina V. Generally, sampler 24 is swabbed along walls of the vagina V to capture cells for analysis. First portion 37 having the cells collected on sampler 24 is removed from the vagina V, deposited inside a standard sized test tube, the test tube is capped, and the collected sample is sent to a laboratory for analysis.

Thereafter, second portion 39 is inserted into the vagina V to collect cervical cells. For example, exo-endocervical sampler 26 is placed in contact with the cervix C such that sampling surface 44 contacts exocervical surface EX and brush 46 enters the cervical os to contact endocervical surface EN.

Textured surface 36 on shaft 22 is available to provide a gripping surface that enables a clinician, for example a clinician wearing gloves, to rotate shaft 22. Rotation of shaft 22 rotates exo-endocervical sampler 26 such that sampling surface 44 sweeps across the exocervical surface EX and brush 46 rotates within and around the endocervical surface EN. In this manner, sampling surface 44 collects cells from exocervical surface EX and looped fibers 70 atraumatically abrades and collects cells from the endocervical surface EN of cervix C. The exo-endocervical cells that are collected are appropriately "smeared" across one or more microscope plates and readied for subsequent laboratory analysis, or alternatively, deposited in a standard wet prep broth container.

In one embodiment, combination exo-endocervical sampling devices described above are selected based upon a status of the patient. For example, one algorithm of use provides that the clinician determines whether the patient is pregnant, and if so selects exocervical sampling device 200 (FIG. 5A). If the patient is not pregnant, the clinician determines if the patient is nulli-parous and/or likely stenotic, and if so employs combination exo-endocervical sampling device 20 (FIG. 1A). In this regard, in the case where the patient is nulli-parous, height H of brush 46 is selected to have a height of about 1.5 cm. If the clinician determines that the patient is parous, the clinician selects combination exo-endocervical sampling device 20 provided with brush 46 having a height H of about 2.0 cm.

Embodiments described above permit the clinician to use one tool to collect both endocervical and exocervical cell samples during a Pap test procedure. This reduces the duration of the office visit, which translates to improved clinic efficiency, and reduces the cost of the instruments used to collect the samples. The looped fibers effectively collect endocervical cell samples without traumatizing the endocervical tissue or the cells. The combination exo-endocervical sampling devices described above permit the clinician to match the device to a given cervix type and sample tissue, which after analysis and diagnosis provides vitally important information useful to the clinician in the early diagnosis of cytopathologic abnormalities and common vaginoses.

In addition to periodically screening for cytopathological abnormalities, clinicians also screen patients for sexually transmitted infections (STI) such as Chlamydia or gonorrhea. When collecting samples to determine if the patient has an STI, it is desirable to collect a sample having a sufficient volume of antigens to reliably indicate the presence of an STI.

A thorough screening for STI in a woman involves collecting a biological sample from the endocervix in addition to a vaginal sidewall discharge sample. When screening a male patient, the clinician typically collects a biological sample from the male urethra. Biological samples for female patients are at times also collected from the female urethra in addition to the vaginal sidewalls. The exo-endocervical sampler 26 described above is not in all cases ideally suited for the collection of samples from the male and female urethras. In addition, it is desirable to collect a sufficient biological sample (a sufficiently high antigen load) in a minimally traumatic manner in a way that minimizes the risk of the STI screen indicating a false negative. For these reasons, it is desirable to use an STI sampling device as described below when screening for sexually transmitted infections.

Figures 11A, 11B:
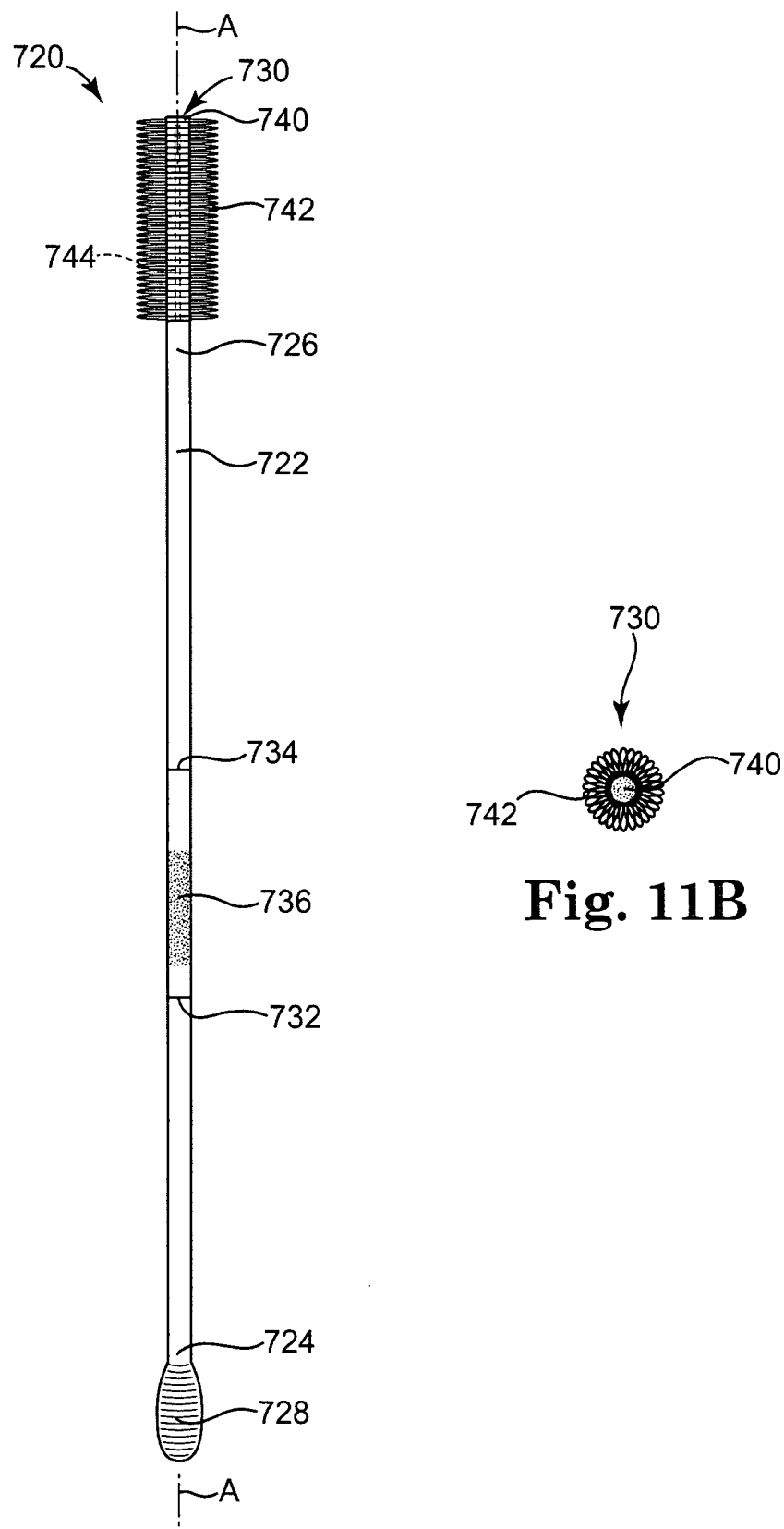
FIG. 11A illustrates a front view of a sexually transmitted infection (STI) sampling device including an absorbent sampler and a wet prep sampler according to one embodiment.
FIG. 11B illustrates a top view of the absorbent sampler shown in FIG. 11A.

FIG. 11A illustrates a front view of a sexually transmitted infection (STI) sampling device 720 according to one embodiment. STI sampling device 720 includes an elongated shaft 722 having a central axis A and defining a first end 724 separated from a second end 726, a wet prep sampler 728 coupled to first end 724, and an absorbent sampler 730 coupled to second end 726. In general, wet prep sampler 728 is configured for collecting a discharge sample from a vaginal sidewall, and absorbent sampler 730 is configured to collect a biological sample from the endocervix or urethra of the female patient.

Shaft 722 is fabricated from a suitable disposable medical-grade plastic, such as a polyolefin. In one embodiment, the elongated shaft 722 includes a first transverse break line 732, a second transverse break line 734, and a textured surface 736 disposed on shaft 722 between first and second break lines 732, 734. Transverse break line 732 is provided to enable a clinician to separate wet prep sampler 728 from absorbent sampler 730. For example, when screening for STIs, the clinician separates wet prep sampler 728 by breaking shaft 722 at first transverse break line 732 and handles the absorbent sample 730 by textured surface 736 provided on shaft 722. Wet prep sampler 728 is controlled by the clinician grasping the attached remaining portion of shaft 722 and swabbing the vaginal sidewalls prior to depositing wet prep sampler 728 into a capped tube for subsequent analysis. Alternatively, where the clinician determines that only a vaginal sidewall discharge sample is needed, the clinician separates wet prep sampler 728 at second transverse break line 734 and handles wet prep sampler 728 by textured surface 736 on shaft 722.

Wet prep sampler 728 is similar to the sampler 24 (FIG. 1A) and the sampler 104 (FIG. 4) described above, and in one embodiment wet prep sampler 728 includes a swab of matted fibers. In other embodiments, wet prep sampler 728 includes a spatula that may optionally include beads or another structured surface configured for collecting a vaginal sidewall sample.

Absorbent sampler 730 includes an absorbent core 740 disposed on the longitudinal axis A of shaft 722, and a plurality of fibers 742 coupled to and extending from absorbent core 740. In one embodiment, absorbent core 740 is disposed along a segment of shaft 722. In another embodiment, absorbent core 740 extends over and along an entirety of a length of shaft 722.

Absorbent core 740 is configured to absorb and capture a biological sample exfoliated from the cervix by fibers 742. In one embodiment, absorbent core 740 includes a foam sponge suited for absorbing liquids. In one embodiment, absorbent core 740 is a uniformly cylindrical core fabricated from an open-cell hydrophilic foam that is disposed about a spindle 744 extending from shaft 722. In one embodiment, absorbent sampler 730 is configured to collect a biological sample from either the endocervix or urethra of the female patient and defines an overall diameter of between about 1-3 mm.

Fibers 742 are coupled to absorbent core 740. Although fibers 742 are illustrated as projecting at a substantially right angle from absorbent core 740, it is to be understood that other configurations of fibers 742 relative to core 740 are also acceptable. Fibers 742 are generally configured to exfoliate a tissue surface to expose a biological sample for collection. In this regard, fibers 742 are configured to capture at least a portion of the exfoliated cells. In one embodiment, fibers 742 include endless looped fibers formed in a cone-shaped brush similar in shape to brush 46 shown in FIG. 1B.

FIG. 11B illustrates a top view of absorbent sampler 730. Absorbent core 740 provides an absorbent plug of material extending along longitudinal axis A. Fibers 742 define an intertwined mat of fibrils around absorbent core 740. The intertwined mat of fibers 742 may be randomly interconnected and arranged, or may be arranged in a more orderly and regular manner. In one embodiment, fibers 742 are similar to the "endless" fiber loops 70 (FIG. 2) and include a multiplicity of endless fibrils defining a void space therebetween configured to capture cells. In one embodiment, fibers 742 include hydrophilic fibers configured to absorb a portion of the biological sample that is exfoliated and/or swabbed from the cervix. In one embodiment, fibers 742 are looped fibers that extend transversely from longitudinal axis A of shaft 722 and are characterized by an absence of a free end.

Figure 11C:
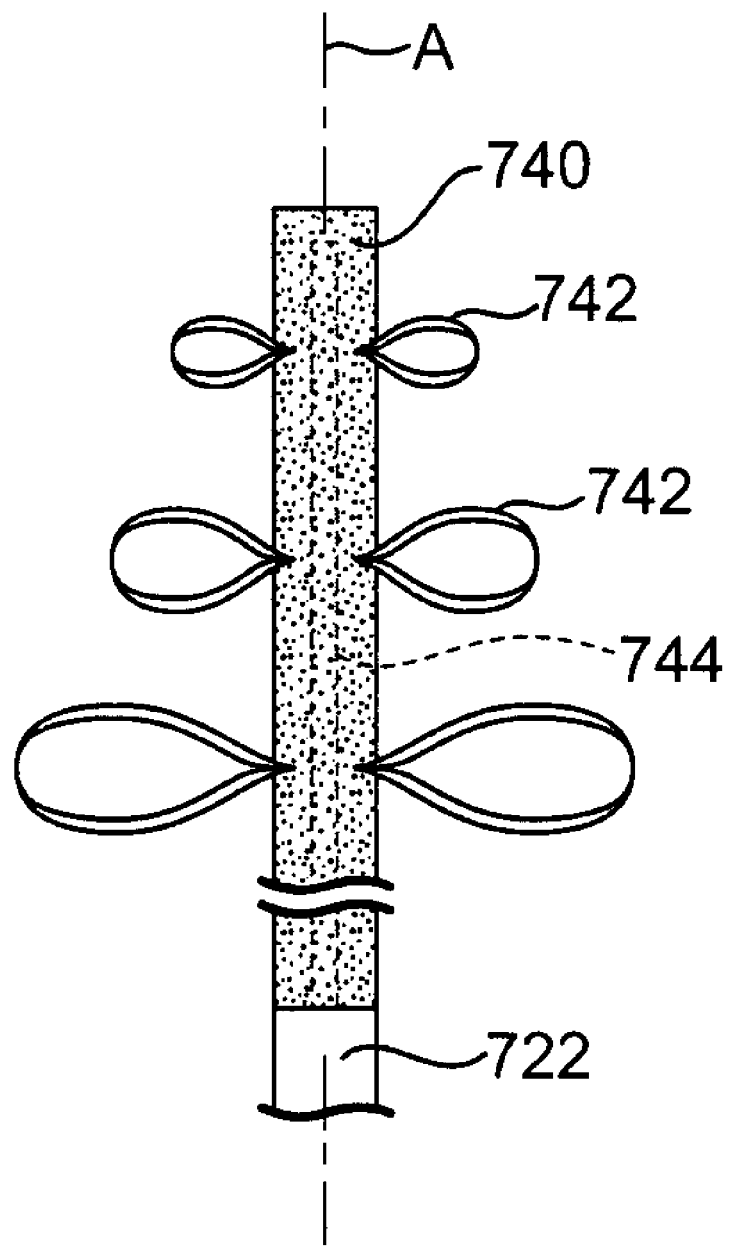
FIG. 11C illustrates a macroscopic view of a portion of the absorbent sampler shown in FIG. 11A.

FIG. 11C illustrates a macroscopic view of a multiplicity of looped fibers 742 coupled to absorbent core 740 forming a plurality of differently sized loops and extending transversely to axis A. In another embodiment, fibers 742 couple to and extend from spindle 744.

In one embodiment, fibers 742 are configured to gently abrade the tissue of the patient and include a low-friction exterior surface. One suitable low-friction exterior surface includes a fluorinated coating applied to fibers 742. One suitable low friction fiber includes fibers 742 fabricated from polytetrafluoroethylene (PTFE). In other embodiments, fibers 742 are configured for gentle abrasion and are fabricated from a flexible polymer material having a suitably small fiber diameter. Exemplary suitable fibers 742 include polyethylene fibers having an average fiber diameter of between about 28-1,000 microns. In other embodiments, fibers 742 include shaped fibers similar to those described above in FIGS. 3A and 3B.

Fibers 742 are configured to gently abrade the tissue surface and exfoliate cells, and both absorbent core 740 and fibers 742 are configured to absorb and capture the exfoliated cells that form a portion of the STI antigen sample. In contrast, the known swabs and samplers employed in STI sampling do not provide an absorbent core, which necessitates more aggressive abrasion to the tissue to ensure that enough biological material is dislodged for possible capture solely by the bristles employed by the known samplers.

Figure 12A:
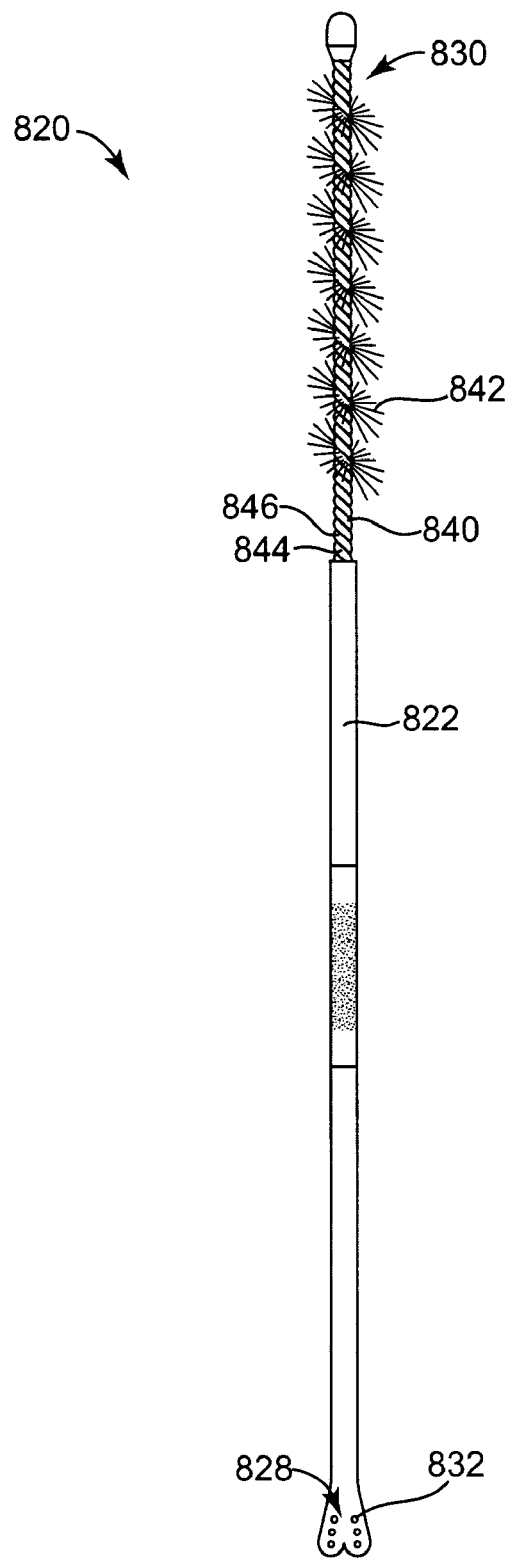
FIG. 12A illustrates a front view of another STI sampling device according to one embodiment.

FIG. 12A illustrates a front view of an STI sampling device 820 according to another embodiment. STI sampling device 820 includes an elongated shaft 822, a wet prep sampler 828 coupled to one end of shaft 822, and an absorbent sampler 830 coupled to another end of shaft 822 generally opposite of wet prep sampler 828.

Shaft 822 is similar to shaft 722 described above. In one embodiment, wet prep sampler 828 defines a spatula including an array of beads 832. In this regard, spatula 828 is similar to spatula 104 described above in FIG. 4, and array of beads 832 is similar to the array of beads 44 described above in FIG. 1C.

Absorbent sampler 830 includes an absorbent core 840 and a plurality of fibers 842 coupled to and extending transversely from absorbent core 840. In one embodiment, absorbent core 840 includes braided absorbent strands 844, 846 that are intertwined to capture fibers 842 between absorbent strands 844, 846. Similar to absorbent sampler 730 (FIG. 11A), fibers 842 are configured to displace cells from the walls of the cervix, and absorbent strands 844, 846 of absorbent core 840 are configured to collect and retain the exfoliated cells for subsequent analysis.

Figure 12B:
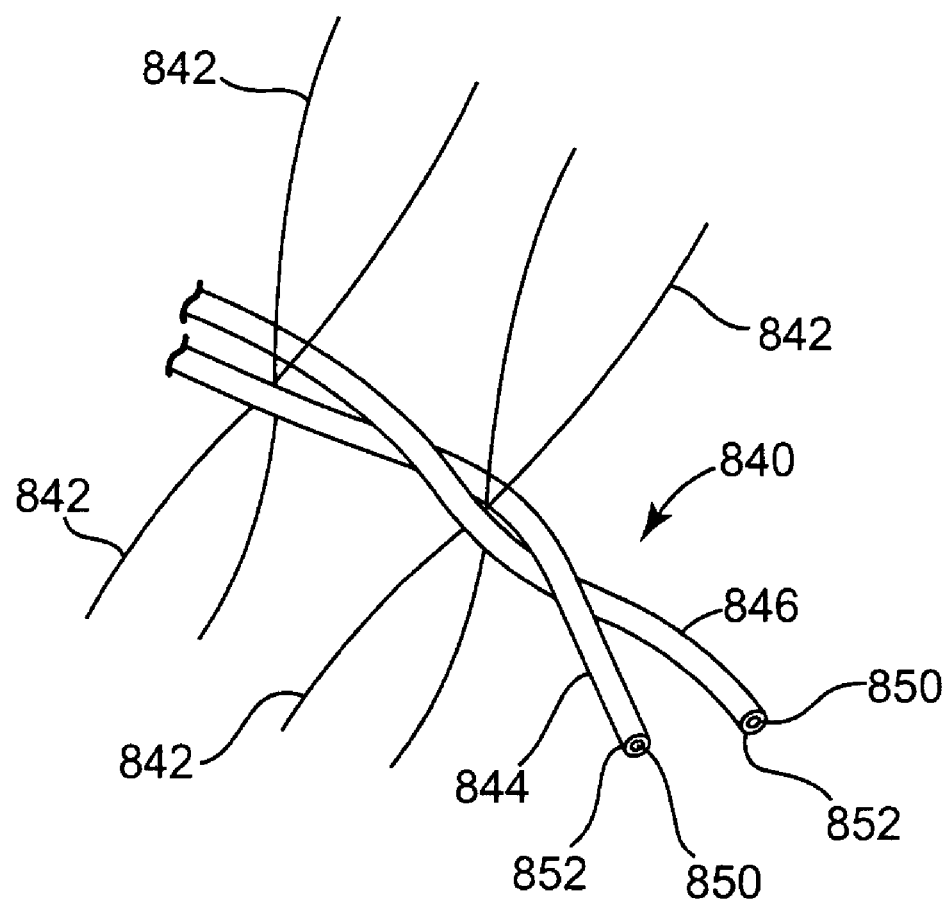
FIG. 12B illustrates a perspective view of a partial cross-section of a portion of an absorbent sampler of the STI sampling device shown in FIG. 12A.

FIG. 12B illustrates a perspective partial cross-sectional illustration of braided absorbent strands 844, 846 slightly separated from one another. In one embodiment, each braided absorbent strand 844, 846 of absorbent core 840 includes a wire support 850 surrounded by an absorbent coating 852. In one embodiment, wire support 850 is a plastic wire support. In alternative embodiments, wire support 850 is a soft metal wire. In one embodiment, absorbent coating 852 includes a hydrophilic polymer deposited over wire support 850. In one embodiment, absorbent coating 852 includes a foam dip-coated or spray coated around wire support 850.

Absorbent core 740 (FIG. 11A) and absorbent coating 852 include generally hydrophilic materials that are configured to absorb at least a portion of the biological sample exfoliated by fibers 742 and 842, respectively. Suitable materials for absorbent core 740 and absorbent coating 852 include hydrophilic polyurethane foams and coating available from Lendell Manufacturing, St. Charles, Mich. Other suitable absorbent coatings and materials are also acceptable and will be recognized by those of skill in the art upon reading this specification.

Fibers 842 include any of the fibers described above, including looped fibers, shaped fibers, hydrophilic fibers, bristles, and low friction fibers suitably configured to gently abrade tissue to enable the collection of cells for STI sampling.

Figure 13:
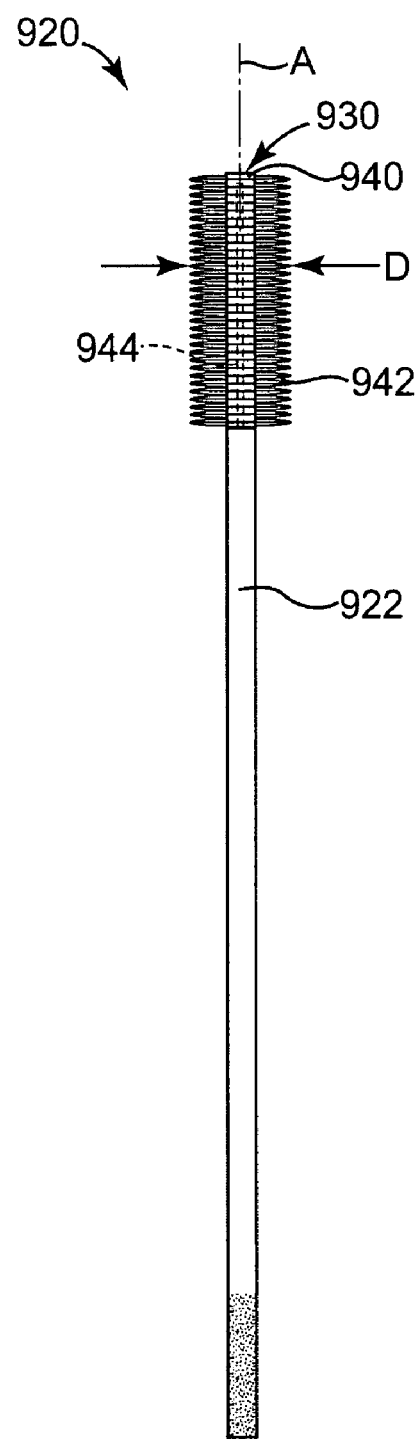
FIG. 13 illustrates a front view of another STI sampling device configured for collecting a biological sample from a male urethra according to one embodiment.

FIG. 13 illustrates a front view of an STI sampling device 920 configured to collect a biological sample from a male urethra according to one embodiment. STI sampling device 920 includes an elongated shaft 922 and an absorbent sampler 930 coupled to shaft 922. Shaft 922 is similar to shaft 722 described above. In one embodiment, absorbent sampler 930 includes an absorbent core 940 disposed on a longitudinal axis A of shaft 922, and a plurality of fibers 942 coupled to and extending in a transverse manner from absorbent core 940. In one embodiment, absorbent core 940 is coupled to a spindle 944 of shaft 922 in a manner that minimizes an overall outside diameter of absorbent sampler 930.

As noted above, STI sampling device 920 is configured to collect a biological sample from a male urethra. With this in mind, an outside diameter D of absorbent sampler 930 is configured to be less than about 2 mm, and preferably less than about 1 mm. Fibers 942 are configured to gently abrade the tissue of the male urethra, and are preferably configured to be soft, flexible, and exhibit a low friction exterior surface. Suitable fibers include, but are not limited to, PTFE fibers, PTFE-coated fibers, polyethylene fibers, and natural fibers. In one embodiment, the average diameter of fibers 942 is between about 20-100 microns, and configured to be minimally abrasive to the sensitive tissue against which the fibers 942 rub.

Absorbent core 940 is similar to the absorbent cores 730 (FIG. 11A) and 830 (FIG. 12A) described above. Although absorbent core 940 is illustrated as an absorbent plug of material, it is to be understood that absorbent core 940 could include braided absorbent strands 844, 846 of absorbent core 840 (FIG. 12A) as described above, provided core 840 is suitably sized for insertion into the male urethra.

Figure 14:
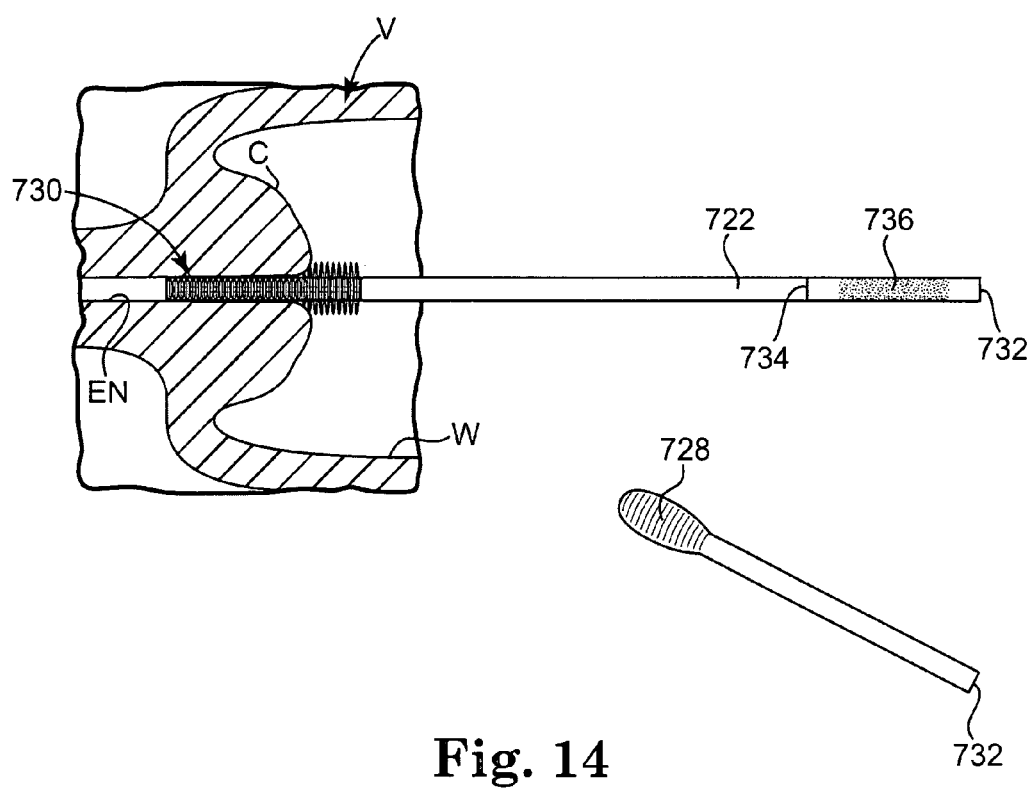
FIG. 14 is a cross-sectional illustration of an absorbent sampler separated from a wet prep sampler, the absorbent sampler employed to collect a cervical sample and the wet prep sampler in a ready position to collect a vaginal sidewall discharge sample according to one embodiment.

FIG. 14 illustrates the collection of an STI sample from a cervix C female patient according to one embodiment. Shaft 722 has been separated at first transverse break line 732 to separate wet prep sampler 728 from absorbent sampler 730. Absorbent sampler 730 is illustrated inserted into the endocervix EN of the patient. With additional reference to FIG. 11A, fibers 742 gently abrade the surface of the endocervix EN and exfoliate cells from the endocervix EN in response to movement (rotation and/or longitudinal) of shaft 722. A portion of the exfoliated cells is captured by fibers 742, and an additional portion of exfoliated cells is captured by absorbent core 740. In this manner, an increased biological loading is captured by absorbent sampler 730 that increases the analytical efficacy of STI screening and minimizes the possibility of a false reading.

Wet prep sampler 728 (separated at the transverse break line 732) is configured for collecting a vaginal discharge sample from a sidewall W of the vagina V. Each of the samplers 728, 730 is sized for and suited for delivery into a broth container for STI analysis. In particular, wet prep sampler 728 is configured to be deposited into a test tube containing broth. Absorbent sampler 730 is configured to smear a portion of the collected sample onto a plate, or alternatively, is configured for depositing into a broth container.

The STI sampling devices described above are configured to capture an increased biological load (antigen loading) in comparison to the cotton swab style of sampler commonly employed in collecting STI samples. Embodiments provide an STI sampling device configured to be more comfortable to the patient during use, and more effective at capturing a sample suitably sized for STI screening.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of gynecological sampling devices. Therefore, it is intended that this invention be limited only by the claims and the equivalents thereof.

What is claimed is:

1. A sexually transmitted infection (STI) sampling device comprising:
   an elongated shaft that defines a first end separated from a second end; and
   an absorbent sampler coupled to the first end of the shaft, the absorbent sampler including:
      a braided absorbent core disposed along a longitudinal axis of the elongated shaft,
      a plurality of fibers extending from the braided absorbent core;
   wherein the plurality of fibers is configured to atraumatically exfoliate cells from a tissue surface of a patient and absorb a first portion of the exfoliated cells, and the absorbent core is configured to absorb a second portion of exfoliated cells not captured by the fibers: and
   wherein the plurality of fibers is configured to atraumatically collect a biological sample in a manner that minimizes risk of an STI screen indicating a false negative.

2. The STI sampling device of claim 1, wherein the absorbent core is disposed along a length of the elongated shaft.

3. The STI sampling device of claim 1, wherein the absorbent core comprises braided absorbent strands, each braided absorbent strand including a wire support surrounded by an absorbent coating.

4. The STI sampling device of claim 3, wherein the absorbent coating comprises an absorbent foam.

5. The STI sampling device of claim 1, wherein the absorbent core comprises an absorbent plug of material, and the plurality of fibers project through the absorbent plug of material.

6. The STI sampling device of claim 1, wherein the fibers comprise hydrophilic fibers configured to absorb cells exfoliated by the fibers.

7. The STI sampling device of claim 1, wherein the fibers comprise substantially non-abrasive fibers including a low-friction fluorinated exterior surface.

8. The STI sampling device of claim 1, wherein the fibers comprise an intertwined mat of interconnecting fibrils.

9. The STI sampling device of claim 1, wherein the fibers are looped fibers including a first closed end opposite a second closed end, the first and second closed ends extending transverse from the longitudinal axis of the elongated shaft and characterized by an absence of a free fiber end.

10. The STI sampling device of claim 9, wherein each looped fiber is a shaped looped fiber that defines a non-circular perimeter in transverse cross-section.

11. The STI sampling device of claim 1, further comprising:
   a wet prep sampler coupled to the second end of the shaft.

12. The STI sampling device of claim 11, further comprising:
   a first transverse break line disposed between the first and second ends, a second transverse break line separated from the first transverse break line, and a textured surface disposed between the first and second transverse break lines.

13. The STI sampling device of claim 11, wherein the wet prep sampler comprises one of a cotton swab and a spatula.

14. The STI sampling device of claim 13, wherein the spatula comprises a staggered array of beads.

15. The STI sampling device of claim 1, wherein the plurality of fibers is configured to atraumatically collect a biological sample in a manner that minimizes risk of an STI screen indicating a false negative.

16. The STI sampling device of claim 1, wherein the braided absorbent core comprises a support surrounded by an absorbent coating.

17. A sexually transmitted infection (STI) sampling device comprising:
    an elongated shaft that defines a first end separated from a second end; and
    a sampler coupled to the first end, the sampler including:
        hydrophilic fibers configured for both exfoliating cells from a tissue surface of a patient and absorbing a first portion of the exfoliated cells,
        a braided core comprising means for absorbing a second portion of exfoliated cells that is provided separate from the hydrophilic fibers.

18. The STI sampling device of claim 17, wherein the means for exfoliating cells comprises looped fibers extending transversely from the elongated shaft.

19. The STI sampling device of claim 18, wherein the means for absorbing exfoliated cells comprises an absorbent material in addition to the looped fibers.

20. A method of collecting a sexually transmitted infection biological sample, the method comprising:
    contacting genital tissue of a patient with an absorbent sampler including an absorbent braided core and a plurality of hydrophilic fibers extending from the absorbent braided core;
    exfoliating cells with the hydrophilic fibers;
    absorbing with the hydrophilic fibers a first portion of the cells exfoliated by the fibers; and
    capturing with the absorbent braided core an additional portion of the cells exfoliated by the hydrophilic fibers.

21. The method of claim 20, wherein capturing with the absorbent core an additional portion of the cells exfoliated by the hydrophilic fibers comprises absorbing a volume of the biological sample with an absorbent foam core of the absorbent sampler.

* * * * *